United States Patent
Bustillos-Cepeda

(10) Patent No.: US 10,653,325 B2
(45) Date of Patent: May 19, 2020

(54) SYSTEM AND METHOD FOR MEASURING ARTERIAL PRESSURE BY ITS EFFECTS

(76) Inventor: Jesus Bustillos-Cepeda, Colonia Lomas de Chapultepec (MX)

( * ) Notice: Subject to any disclaimer, the term of this patent is extended or adjusted under 35 U.S.C. 154(b) by 509 days.

(21) Appl. No.: 12/866,854

(22) PCT Filed: Jan. 12, 2010

(86) PCT No.: PCT/MX2010/000003
§ 371 (c)(1),
(2), (4) Date: Oct. 3, 2011

(87) PCT Pub. No.: WO2011/087347
PCT Pub. Date: Jul. 21, 2011

(65) Prior Publication Data
US 2012/0022383 A1 Jan. 26, 2012

(51) Int. Cl.
*A61B 5/02* (2006.01)
*A61B 5/022* (2006.01)

(52) U.S. Cl.
CPC ...... *A61B 5/02208* (2013.01); *A61B 5/02225* (2013.01)

(58) Field of Classification Search
CPC .................................................. A61B 5/022
USPC ................................................. 600/490–499
See application file for complete search history.

(56) References Cited

U.S. PATENT DOCUMENTS

| | | | | |
|---|---|---|---|---|
| 1,982,505 A | * | 11/1934 | Emerson | A61B 5/0235 600/499 |
| 3,744,490 A | * | 7/1973 | Fernandez | A61B 5/02208 600/496 |
| 4,326,536 A | * | 4/1982 | Kitagawa et al. | 600/495 |
| 4,873,987 A | * | 10/1989 | Djordjevich | A61B 5/022 600/485 |
| 5,103,830 A | * | 4/1992 | Shinomiya | A61B 5/02208 600/485 |
| 5,533,511 A | * | 7/1996 | Kaspari | A61B 5/02007 128/925 |
| 5,651,369 A | * | 7/1997 | Tomita | A61B 5/02208 600/493 |

(Continued)

FOREIGN PATENT DOCUMENTS

JP 08280641 A 10/1996

OTHER PUBLICATIONS

Allen, John. "Photoplethysmography and its application in clinical physiological measurement." Physiological Measurement. vol. 28. Feb. 20, 2007. R1-R39.*

(Continued)

*Primary Examiner* — Eric J Messersmith
(74) *Attorney, Agent, or Firm* — Notio Law Group, LLC

(57) ABSTRACT

The system and method for measuring arterial pressure by its effects consists of a six-stage procedure and three devices; the procedure to indirectly measure diastolic arterial pressure controls the tasks of a first device applying a measured gradual external contact force, a second sensor device of arterial that records arterial expression, and a third device which is a device to measure and detect the arterial cycle diastolic and systolic period in order to provide the diastolic arterial pressure value using an indirect method. Additionally, systolic arterial pressure is measured with no overpressure due to heartbeats produced after arterial occlusion.

14 Claims, 10 Drawing Sheets

(56) References Cited

U.S. PATENT DOCUMENTS

2010/0106029 A1*  4/2010  Fraden ............... A61B 5/02208
                                                600/493
2011/0295129 A1*  12/2011 Tooley .................. A61B 5/022
                                                600/490

OTHER PUBLICATIONS

Maley, Cindy. "Intro to Blood Pressure." American Diagnostic Corporation. http://adctoday.com/blog/intro-blood-pressure.*

"Korotkoff Sounds." https://en.wikipedia.org/wiki/Korotkoff_sounds.*

Sowa, et al. "Review of near-infrared methods for wound assessment." Journal of Biomedical Optics. vol. 21(9). Sep. 2016.*

* cited by examiner

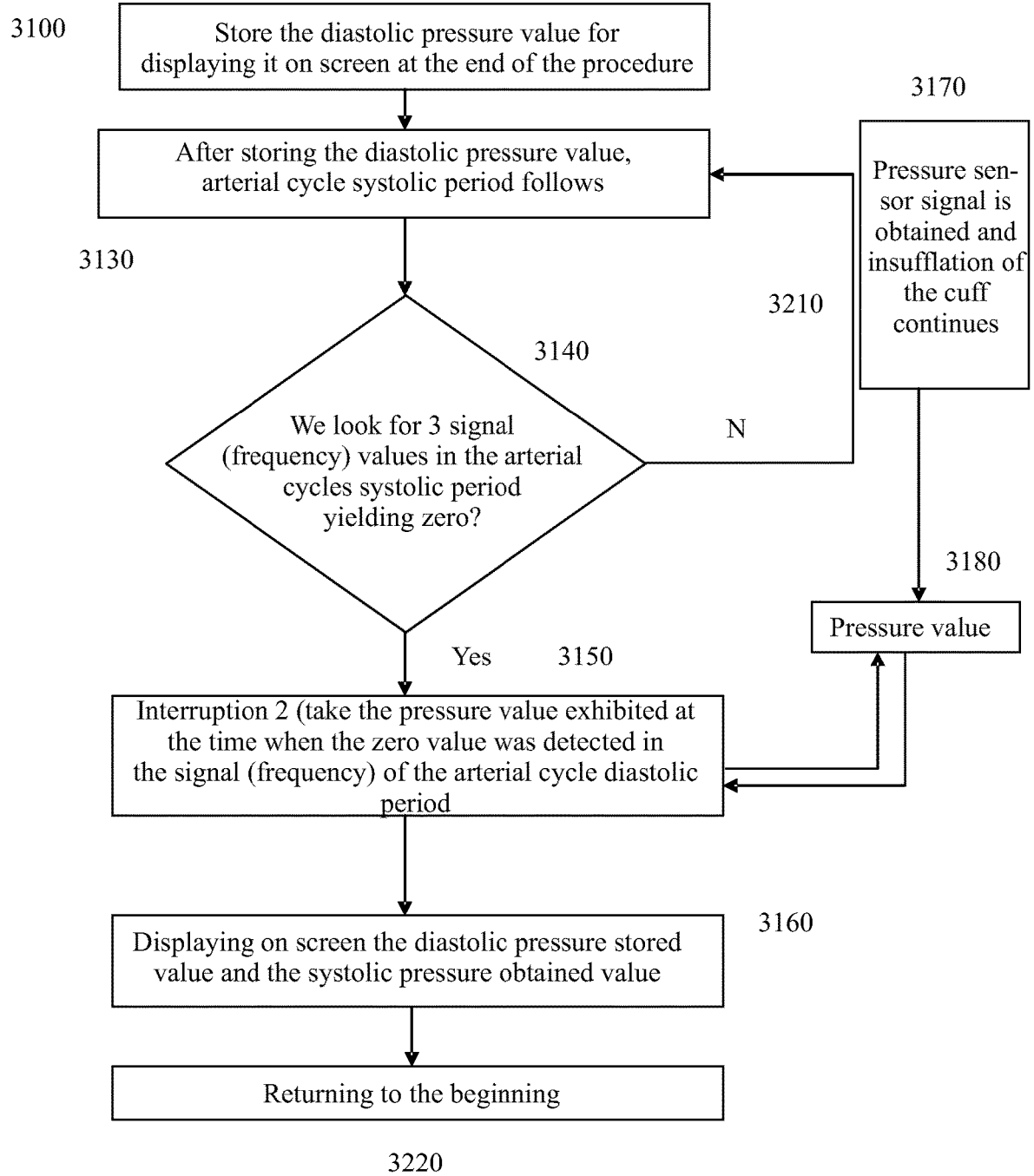
CONTINUATION OF FIG. 13

SYSTEM AND METHOD FOR MEASURING ARTERIAL PRESSURE BY ITS EFFECTS

FIELD OF THE INVENTION

The present invention refers to the systems, procedures, and instruments designed in the field of medicine and Biomedical Engineering and which are used in medicine to measure arterial blood pressure. More particularly, it refers to an indirect measurement system and procedure of diastolic arterial pressure based on the effects of the arterial cycle diastolic period.

BACKGROUND OF THE INVENTION

Arterial pressure is the force applied by blood on arterial walls. In order to measure such a pressure, the force unit applied by blood is divided by the arterial wall area unit and the resulting measure is the pressure unit, for instance mmHg or pascals.

Arterial blood force is the pressure applied by blood to the arterial wall, and the measure results from the blood pressure unit multiplied by the arterial segment wall area unit. Its units are dynes or Newtons.

Cardiac cycle is the set of events related to the blood flow that must occur from the beginning of a heartbeat to the beginning of the next one. Every heartbeat includes two main stages in ventricles: The ventricle systole and diastole. The term diastole means muscle relaxation. Throughout the cardiac cycle, blood pressure increases and decreases in heart and arterial system. The variation of pressure in arteries has two stages: the systolic blood pressure time which is short and a longer time corresponding to the diastolic blood pressure.

Arterial cycle is the unit for the variation of repetitive physical properties of the artery depending on time, which consists of the events of the blood flow and arterial wall in a higher blood movement period referred to as systolic period and a lower blood movement period referred to as diastolic. As shown in the dissertation "*EL CICLO ARTERIAL*" *Universidad Autónoma de Tamaulipas, Mexico, Facultad de Medicina de Tampico* to obtain the Master of Science degree with specialization in Medical Urgencies, from Jesús Bustillos Cepeda, which has not been published due to the prosecution of the subject patent application. With respect to the amount of pressure of the artery during systolic and diastolic stages, the systolic blood pressure is the highest pressure from the two stages and has blood flow all throughout the stage; while the diastolic blood pressure is the lowest pressure from the two stages and its blood flow does not always last the full arterial cycle diastolic time.

To obliterate: To obstruct or close a conduit or cavity.

Measurement of diastolic arterial pressure through arterial obliteration by applying a gradual external contact force: It is the action of applying a gradual external contact force until obliterating an artery to measure the force applied by the blood on the arterial wall in the diastolic period.

To clear: To remove something that obstructs another thing.

Measurement of diastolic arterial pressure through arterial clearing by removing the gradual external contact force: It is the action of removing the gradual external contact force until an artery has been cleared in order to measure the force applied by the blood on the arterial wall in the diastolic period.

Measurable artery: Arterial segment which is used to know the measurement of a magnitude.

Measurable artery: In the present invention; an arterial segment used to know the pressure measurement applied by blood on its wall area unit.

Parameter: is the numerical value or fixed data that is considered in the study or analysis of a certain issue.

In the present application, a parameter is a sample of blood flow and arterial wall expressions without being affected by the external force applied. Such values shall be taken into consideration to calculate systolic and diastolic arterial pressure.

Arterial pressure can be measured in an invasive (direct) manner, which is not relevant for this document, or in a non-invasive (indirect) manner.

Measuring diastolic and systolic arterial pressure using an indirect method is essential for this invention and in the state of the art such measuring is performed using the auscultatory method and the oscillometric method, which have their origin, description and scientific foundations on the following historical facts:

Auscultatory Method (Classic Method):

1896: Development of blood pressure measurement indirect method by Von Riva Rocci Recklinghaus who, literally, states: " . . . the instrument I have developed measures in a manometric fashion the force that is required to stop the pulse wave progression; sphigmomanometry is performed in one of the major branches of the aorta artery, on the humeral artery, which is a direct continuation of the axillary one, in such a manner that the measurement estimates the full load in a point that is very near to the aorta artery, almost inside the same . . . "

1905: The Von Riva Rocci Recklinghaus technique is improved by the addition of auscultation by a Russian surgeon, Nikolai Sergeyevich Korotkoff who, in his dissertation from the Imperial Academy of Military Medicine in Saint Petersburg in 1905, described the sounds heard using a stethoscope placed on the brachial artery under the Von Riva Rocci Recklinghaus cuff during slow deflation, which literally states in a translation from Russian to English language: " . . . The cuff of Riva—Rocci is placed on the middle third of the upper arm; the pressure within the cuff is quickly raised up to complete cessation of circulation below the cuff. Then, letting the mercury of the manometer fall one listens to the artery just below the cuff with a children's stethoscope. At first no sounds are heard. With the falling of the mercury in the manometer down to a certain height, the first short tones appear; their appearance indicates the passage of part of the pulse wave under the cuff. It follows that the manometric figure at which the first tone appears corresponds to the maximal pressure. With the further fall of the mercury in the manometer one hears the systolic compression murmurs, which pass again into tones (second). Finally, all sounds disappear. The time of the cessation of sounds indicates the free passage of the pulse wave; in other words at the moment of the disappearance of the sounds the minimal blood pressure within the artery predominates over the pressure in the cuff. It follows that the manometric figures at this time correspond to the minimal blood pressure . . . "

Oscillometric Method:

1940 Report of the "self-monitoring" concept and its differences with arterial pressure measurements in the doctor's office (Ayman and Goldshine); 1969 Theoretical demonstration of the oscillometric principle (Posey); 1970 Oscillometry clinical applications (MAPA and AMPA). The oscillometric method is used by most non-invasive automated devices. One limb and its vasculature are compressed in one arm by an inflatable condensation cuff. The simplified measurement principle from the oscillometric method is an amplitude measurement of pressure change in the cuff. As the cuff is inflated onr systolic pressure, the amplitude suddenly increases with pulse breaks through occlusion. This is very close to the systolic pressure. When cuff pressure is reduced, the amplitude pulse increase reaches its maximum threshold and then quickly decreases. The diastolic arterial pressure index is taken when this transition begins. Therefore, systolic and diastolic blood pressure is obtained by identifying the region in which there is, respectively, a rapid increase and a reduction in pulse amplitude. Medium arterial pressure is found in the point of the maximum oscillation.

The instruments that are used to observe arterial expressions being depicted by Korotkoff are the stethoscope, pressure sensor, flow sensor and sphygmomanometer with respect to a manometer, in order to determine arterial pressure. In the methods to measure arterial pressure in the state of the art, measurements are performed by observing the expressions that have been previously depicted by Korotkoff in his dissertation. In the state of the art, arterial pressure measurement is ruled by the Korotkoff's method in which, in order to measure arterial pressure, the following steps are followed: 1) The humeral artery is pressed against the humeral bone through the pneumatic cuff; 2) the time in which the pressure being applied closes the arterial flow is detected; 3) once the artery has been occluded, pulse wave expressions are not observed anymore and pressure is applied beyond the occlusion point; 4) then the cuff pressure is reduced by opening the valve that is found in the insufflation bulb; 5) the pulsatile blood flow reappearance through the partially compressed artery results in Korotkoff's sounds (sounds resulting from the arterial pulse wave produced by systolic pressure when arriving to the partially occluded artery); 6) when the first Korotkoff's sound appears, the pressure level at the cuff indicates systolic arterial pressure, also referred to as "Korotkoff sounds' stage I" and which is the maximum pressure generated by the pulse wave during each cardiac cycle; 7) the pressure applied on the artery continues to be reduced, permanent disappearance of Korotkoff's sounds indicates diastolic arterial pressure magnitude, since laminar blood flow restoration in the artery eliminates Korotkoff's sounds, such sound elimination being observed in stage V from Korotkoff's sounds classification.

The five Korotkoff's sounds are classified by stages in the state of the art:

Stage I: indicates that vessel pressure has exceeded external pressure, being a sudden, loud and progressively intense sound corresponding to systolic arterial pressure.

Stage II: the sound is more intense, lengthy, and more clear.

Stage III: the sound continues to be loud and clear, although a murmur begins to be perceived which indicates its proximate disappearance.

Stage IV: there is a sudden loss of sound intensity, which becomes markedly muffled with a continuous murmur; it is sometimes the last thing which is heard and some authors determine diastolic blood pressure in this stage.

Stage V: sound fully disappears when laminar flow is restored. World Health Organization advises that diastolic arterial pressure shall be measured in this stage.

The oscillometric procedure is the measure based on amplitude oscillations resulting from the pressure change inside a force application device. It also depends on Korotkoff's observations to measure arterial pressure, as its name indicates, the method uses the oscillometer, which is an electronic device based on the pulse wave analysis. In such oscillometric method, the individual's arm is compressed by an inflatable condensation cuff, such that the measurement is based on the pressure change amplitude in the cuff. Therefore, when such a cuff is inflated on systolic pressure, the amplitude suddenly increases with pulse rest periods through occlusion, that is, very near to systolic pressure. When cuff pressure decreases, amplitude pulse increase reaches a maximum threshold and then rapidly decreases. Diastolic pressure index is taken when this transition begins. Therefore, systolic and diastolic blood pressures result from identifying the region in which there is a sudden increase and then a decrease in the amplitude of systolic pulses.

According to background scientific evidence, it is seen that, by using the procedures and devices in the state of the art to indirectly measure arterial blood pressure, it is only possible to measure systolic arterial pressure in two points: The first one is blood systolic pressure when overcoming the force applied to the measurable artery and the second one is the pressure in the cuff when it is not able anymore to affect blood systolic pressure. The latter pressure is referred to as diastolic arterial pressure, which is not accurate. Measuring systolic arterial pressure using Korotkoff's method does determine in fact systolic arterial pressure, but including the error corresponding to pressure overload that heartbeats occurring after occlusion produced in the occluded artery. The second systolic pressure phenomenon, which is mistakenly known as diastolic arterial pressure, is determined by using the state of the art methods and instruments. Such a measurement consists of measuring the pressure applied by the cuff to the arm at the time in which Korotkoff's sounds disappear, since the pressure applied using the cuff decreases to a point at which it does not affect anymore the blood flow of the major systolic pulse wave, allowing that the turbulent systolic arterial blood flow becomes a laminar flow and thus it does not result in expressions (Korotkoff's sounds). In spite of being clearly a phenomenon of the systolic arterial pressure, it has been usually determined that this measurement corresponds to diastolic arterial pressure.

In the state of the art, diastolic arterial pressure is defined as "the lowest value from both arterial blood pressures values, which corresponds to arterial blood pressure when heart is in a diastolic or resting state".

According to the above, it may be seen that, in the state of the art, procedures and devices to measure arterial blood pressure in a non-invasive manner, exhibit a major disadvantage: although they try to measure indirect diastolic arterial pressure, they do not manage to do so. Therefore, the state of the art exhibits a scientific gap, since there are no methods or instruments measuring diastolic arterial pressure using an indirect method! This is due to the fact that "What exists in the state of the art to measure diastolic arterial pressure are methods and instruments to measure the minor external contact force applied using a device on the artery at the time in which systolic arterial pressure is not able anymore to produce Korotkoff's sounds resulting from arterial wall vibrations and blood flow turbulences corresponding to systolic arterial pressure". Along with the above, by using the instruments and procedures found in the state of the art, the only way of measuring diastolic arterial pressure is by using an invasive method (intra-arterial catheter).

The present invention aims to solve some of the following problems in the auscultatory method (classic method): the indirect Von Riva Rocci Recklinghaus' method to measure arterial blood force that is literally stated as follows: "the instrument I have developed measures in a manometric fashion the force that is required to stop the pulse wave progression; sphigmomanometry is performed in one of the major branches of the aorta artery, on the humeral artery, which is a direct continuation of the axillary one, in such a manner that the measurement estimates the full load in a point that is very near to the aorta artery, almost inside the same" . . . .

Comments on Von Riva Rocci's principle: Under normal conditions, the artery exhibits a flow having a pressure and force determined before ventricular ejection, referred to as diastolic pressure. This pressure is ignored by Von Riva Rocci in his description! Such an arterial blood diastolic pressure is suddenly interrupted by the blood volume which is ejected by the heart to the artery in a short period of time, resulting in a higher blood pressure and force which provokes an expansion of the artery which is referred to as arterial pulse wave. Von Riva Rocci Recklinghaus' technological and scientific contribution is an instrument and procedure to manometrically measure the force required to stop the pulse wave progression, that is, the systolic force or pressure, since this is the one generating such a wave.

The above results in the problematic fact that Riva Rocci did not determined the measurement of diastolic arterial pressure by using an indirect method.

Later on, Von Riva Rocci Recklinghaus' technique is improved with the addition of auscultation made by the Russian surgeon Nikolai Sergeyevich Korotkoff, who states the following in its dissertation: " . . . With the further fall of the mercury in the manometer one hears the systolic compression murmurs, which pass again into tones (in second place). Finally, all sounds disappear. The time of the cessation of sounds indicates the free passage of the pulse wave; that is, at the moment of the disappearance of the sounds the minimal arterial pressure within the artery predominates over the pressure in the cuff. It follows that the manometric reading at this time corresponds to the minimal arterial pressure".

Korotkoff refers to the artery producing short tones that their aspect indicates part of the pulse wave, when he states " . . . the manometric reading continues . . . ", he means that the deflation phenomenon continues and thus the decrease of the pressure applied to the arm by the cuff, as well as that the first tone that appears as a full tone compared to the preceding ones corresponds to the maximum pressure. As seen in the description, maximum pressure results from measuring the external force with the appearance of the first full tone after an actual occlusion and force release resulting from deflation. This technique does not consider the phenomenon that the time on which occlusion is observed includes several cardiac cycles with no tone expression and that every cardiac cycle produces a volume defined by the upper end of humeral artery, which shall allow the fluid passage for the irrigation of the arm, forearm, and hand. Nevertheless, due to the arterial occlusion produced by the cuff due to preventing blood flow passage, volume and pressure are increased in the artery segment located before the artery segment being occluded. This provokes that, when measuring external force guided by the appearance of Korotkoff's first tone, blood pressure magnitude is altered by blood overload due to ventricular ejections occurred after the artery is occluded. The following problem results from the above: how to measure systolic arterial pressure using an indirect method without affecting pressure overload, resulting in ventricular ejections after the artery is occluded?

When describing tones to determine diastolic pressure using an indirect method, Nikolai Sergeyevich Korotkoff states " . . . With the further fall of the mercury in the manometer one hears the systolic compression murmurs, which pass again into tones (in second place). Finally, all sounds disappear. The time of the cessation of sounds indicates the free passage of the pulse wave; that is, at the moment of the disappearance of the sounds the minimal arterial pressure within the artery predominates over the pressure in the cuff. It follows that the manometric reading at this time corresponds to the minimal arterial pressure".

And he is right when he states that the sounds disappearing at the end due to cuff deflation are systolic sounds, since pulse is the effect produced by the expansion of the artery as a result of ventricle ejection during cardiac systole. The force applied by the cuff results from reducing the volume in a concentric direction and the highest and lowest forces to be measured in the artery are in an eccentric direction. When the external force occludes the artery and occlusion is progressively released by deflation, the force generating the lowest volume in the artery shall not be affected anymore and finally when the external force applied by deflation falls even more it shall not affect anymore the highest or systolic force, which will emit the last tones depicted by Korotkoff. When tones disappear, diastolic arterial pressure is determined based on arterial expressions due to the relationship between the cuff force and the artery with systolic arterial pressure, and not diastolic arterial pressure actual value!

The above shows that, as it is natural, the lowest or diastolic pressure measurement using Korotkoff's method is made based on systolic arterial pressure effects.

The following problem arises from the above: how to measure diastolic arterial pressure with an indirect method based on its effects and not on the effects resulting from systolic arterial pressure?

SUMMARY OF THE INVENTION

In order to overcome the problems of the procedures and devices found in the state of the art to measure diastolic arterial pressure using an indirect method, this novel system and method for measuring arterial pressure by its effects measures diastolic and systolic arterial pressure based on the expression from the artery in the arterial cycle systolic and diastolic period, respectively. Arterial cycle is defined as the repetitive physical variation unit of the artery along time, which consists of the arterial wall and blood flow events which are defined in two periods. The first period with a short time, more movement, and more blood pressure is referred to as systolic arterial pressure period. The second period with a time higher than the preceding one, less movement and less blood pressure is referred to as diastolic blood pressure period.

In order to overcome the first problem: how to measure diastolic arterial pressure using an indirect method based on its effects and not on the effects resulting from systolic arterial pressure?

The present invention measures diastolic arterial blood pressure by observing arterial wall and blood flow expressions which are created or eliminated in the arterial cycle diastolic period by applying a gradual contact force on the measurable artery.

In order to overcome the second problem: how to determine systolic arterial pressure using an indirect method without affecting blood pressure overload resulting in ventricular ejections after the artery is occluded?

The present invention furthermore provides a procedure for measuring systolic arterial pressure by using an indirect method in the arterial cycle systolic period and without affecting the blood pressure overload resulting in ventricular ejections after the artery is occluded. In this novel invention, systolic arterial pressure is furthermore measured based on the effects created or eliminated by obliterating the artery by applying an increasing external contact force, recording and measuring the expressions that are generated by the flow, arterial wall, and manometer in the arterial cycle systolic period at the time of equaling the external force applied with the blood force on the arterial wall.

Objects of the System and Method for Measuring Blood Pressure by its Effects

Considering that the state of the art does not provide a method and instruments able to measure diastolic arterial pressure using an indirect method, it is an object of the present invention providing a system and method for measuring arterial pressure by its effects, which is very simple and highly effective to measure diastolic arterial pressure using an indirect method.

Another object of the present invention is providing a procedure that is able to measure diastolic arterial pressure in a sensitive and specific manner using an indirect method.

Another object of the present invention is providing a system and method for measuring arterial pressure by its effects that is able to measure systolic arterial pressure by its effects on the arterial cycle systolic period and diastolic arterial pressure by its effects on the arterial cycle diastolic period using an indirect method.

A further object of the present invention is providing a procedure to measure diastolic arterial pressure by the effects generated by diastolic arterial pressure by applying an external contact force using a device applying a measured gradual external contact force, by observing the phenomena produced by arterial wall and blood flow with a blood expression sensor. These two elements being the data information source for a device measuring and detecting the arterial cycle diastolic and systolic periods which discriminates between the systolic and diastolic periods in an arterial cycle in order to determine diastolic and systolic arterial pressure by their effects.

A further object of the present invention is providing a device measuring and detecting arterial cycle diastolic and systolic periods which, in one embodiment, is an electronic motherboard discriminating between the diastolic and systolic periods in an arterial cycle in order to determine, respectively, diastolic and systolic arterial pressures by their effects.

A further object of the present invention consists of providing a procedure to more accurately measure systolic arterial pressure without the overpressure resulting from heartbeats occurring after occluding the measurable artery.

Advantages of the Present Invention

The advantages of this invention consist of indirectly measuring for the first time in history diastolic arterial pressure by its effects. By doing this, we will be able to measure, by using an indirect method, the blood pressure exhibited by the artery when the heart begins ventricular ejection and the heart has to overcome said pressure in every heartbeat in order to empty its ventricle blood content to the arterial. This will allow improving the diagnosis and treatment of a great number of heart and artery diseases, mainly heart failure diseases. A further advantage of this inventive measurement system is that it contributes to health sciences a procedure and instrument to indirectly measure diastolic arterial pressure. This is relevant for human beings since, "for every increase of 20 mmHg of systolic pressure or 10 mmHg of diastolic pressure, the risk of dying due to a heart disease or brain attack doubles in human beings."

Scientific Basis:

In the state of the art and postulates in the dissertation "El Ciclo Arterial" from Universidad Autónoma de Tamaulipas, Mexico, Facultad de Medicina de Tampico by Jesús Bustillos Cepeda, a document which has not been published due to the prosecution of the subject patent application, the following is stated: "An artery is composed of 3 elements: Wall, internal cross section area and blood flow. The arterial system starts in the joint of the aortic valve with the left ventricle, while it ends in capillaries. Under ideal and basal conditions of arterial system there are two kinds of blood distribution energy: The arterial distension energy distributing 40% of the volume being introduced in 0.2 seconds, which results from ventricular ejection and artery adaptation response; and the arterial contraction energy distributing 60% of the remaining volume in 0.6 seconds, which results from the potential resilient energy from the arterial wall. Ventricular ejection is cyclical and affects all the blood volume in the arterial system from the aorta artery to the capillary depending on the pressure wave speed." Due to the above and with respect to the abovementioned dissertation it is stated that: "Cyclical ventricular ejection results in cyclical arterial responses" and an arterial cycle is produced always in response to an effective ventricular ejection of the cardiac cycle. Due to the above, the arterial cycle is defined as a continuous phenomenon in which the variation of periodical physical magnitude movement in the artery is performed. Due to the arterial distension energy resulting from the ventricular ejection and the artery adaptation response in a rapid stage (distension or filling up; 25% of the arterial cycle lasting time). And the arterial contraction energy resulting from the resilient potential energy of the arterial wall in the slow stage (contraction or emptying; 75% of the arterial cycle lasting time). Pressure slow fall in the emptying stage is suddenly interrupted by the onset of the filling up stage and by the rapid pressure increase, whereby the process starts again. During a full arterial cycle, arteries experience a rapid volume increase until reaching a maximum pressure point (rapid or distention stage), as an adaptation response to blood volume increase, and a slow decrease of pressure fall (slow or contraction stage), in which the highest percentage of volume distribution is performed by resilient recovery and as a capillary resistance response.

BRIEF DESCRIPTION OF THE DRAWINGS

The novel aspects considered to be characteristic of the present invention, will be established more particularly in appended claims. However, the invention of an electronic device to measure indirect arterial blood pressure, both regarding its configuration and operating method, along with other objects and advantages of the same, shall be better understood in the following detailed description in connection with the appended drawings, wherein:

FIG. 1 shows the first stage of arterial expressions without diastolic and systolic arterial pressure being affected.

FIG. 2 shows the second stage of arterial expressions only affecting systolic arterial pressure.

FIG. 3 shows the third stage of arterial expressions, diastolic pre-occlusion or overcoming of the diastolic flow pressure to occlusive external force.

FIG. 4 shows the fourth stage of arterial expressions, in which the flow with diastolic arterial pressure is occluded and only the flow with systolic pressure is affected.

FIG. 5 shows the fifth stage of arterial expressions, in which systolic arterial pressure is affected and there is diastolic occlusion, which is the systolic pre-occlusive stage.

FIG. 6 shows the sixth stage of arterial expressions, with full occlusion of systolic and diastolic arterial flow.

DETAILED DESCRIPTION OF THE INVENTION

Figure 1:
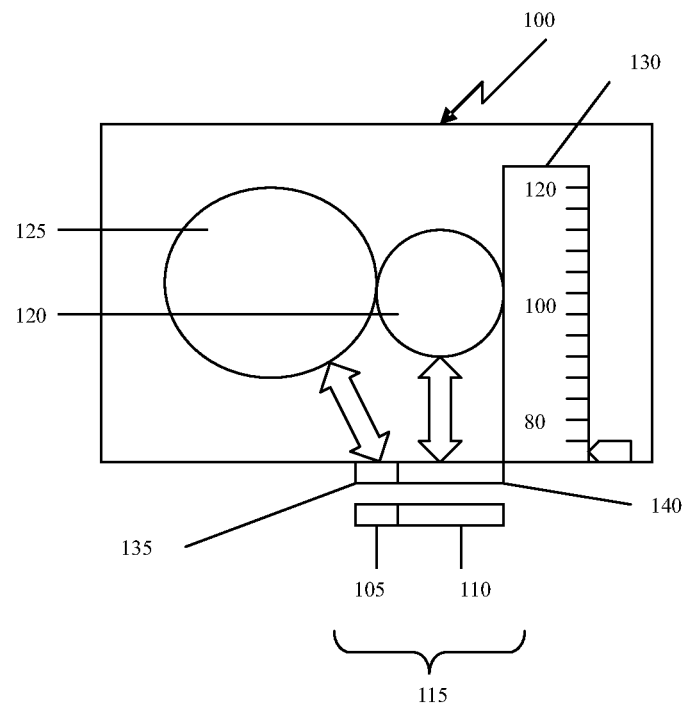
FIGS. 1 to 6 schematically show the various stages of blood expressions occurring when applying an external contact force on a measurable artery.

Specifically with respect to appended drawings and, more particularly, to FIGS. 1 to 6, they show the various stages of arterial expressions when applying an increasing external contact force to the artery. Those stages are depicted as follows:

FIG. 1 shows a first stage 100 without affection of systolic period 105 and diastolic period 110 of the arterial cycle 115, in which there is no affection caused by an external force on blood flow forces or on arterial wall forces. In such a first stage 100 arterial blood flow or volume is not affected, referring to the lowest artery blood flow or volume 120 and to the highest artery blood flow or volume 125, wherein an applied force or pressure indicator 130 indicates "zero". The highest artery blood flow 125 occurs in the lowest time 135 during the highest blood flow force and pressure of the systolic period 105, taking up the 25% of the arterial cycle 115. The lowest artery blood flow 120 occurs in the highest time 140 during the lowest blood flow force and pressure of the diastolic period 110, taking up the 75% of the arterial cycle 115.

Figure 2:
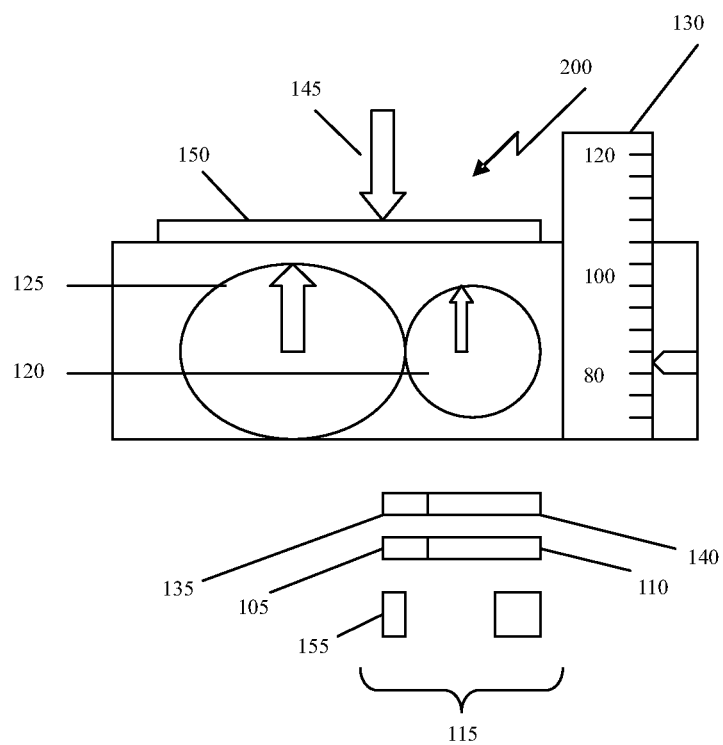

FIG. 2 shows a second stage 200 corresponding to the affection of systolic period forces 105 of arterial cycle 115, without affecting the diastolic period blood forces 110. FIG. 2 shows the second stage 200 in which artery blood volume or flow is already affected, being shown that the force or pressure being applied 145 has a certain magnitude on a defined area 150 recorded in the force indicator 130 with a value of "20". The highest blood flow or volume 125 of the artery shows expressions, since systolic period flow 105 changes, wherein such expressions refer, among other things, to a sound 155 that is detected with sensors. The lowest blood flow or volume 120 shows no changes.

Figure 3:
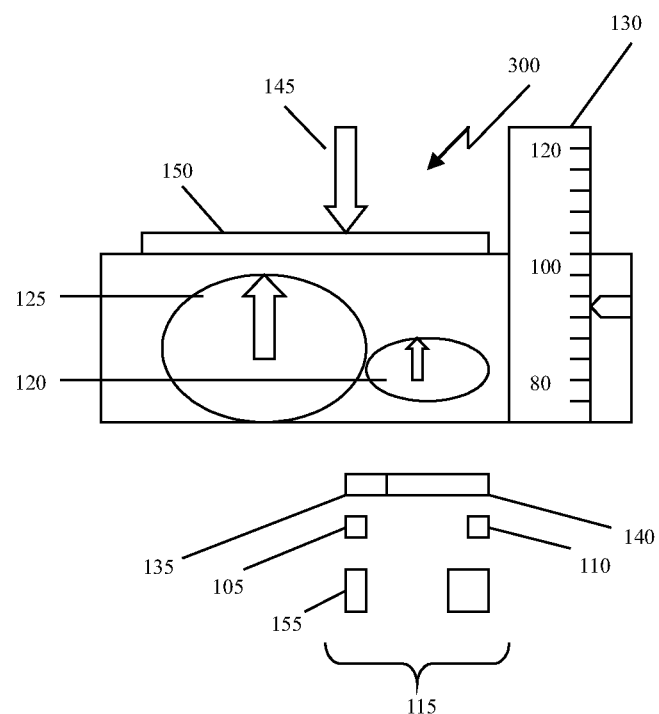

FIG. 3 shows a third stage 300 with affection of the systolic 05 and diastolic 110 periods of the arterial cycle 115 (diastolic pressure pre-occlusion). In such a stage 300 the highest and lowest pressures of the corresponding periods are affected. In this third stage 300, the force or pressure being applied 145 has a magnitude on the defined area 150 that is recorded in the force indicator 130 with a value of "40". The highest blood flow or volume 125 shows expressions since the systolic period 105 changes, wherein such expressions refer to a sound 155. The lowest blood flow 120 shows expressions since the volume in the diastolic period 110 is affected.

Figure 4:
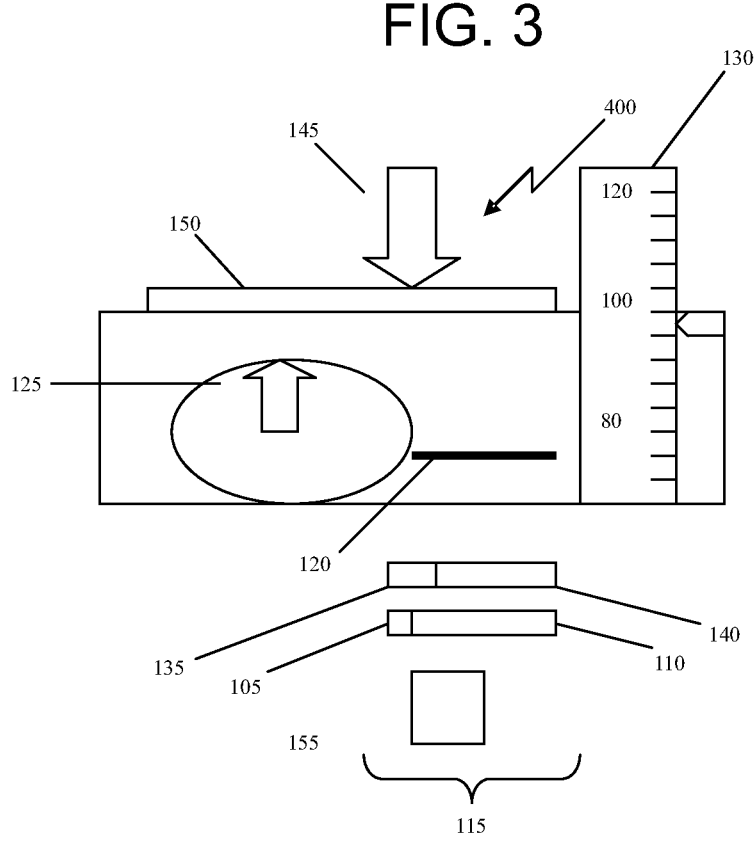

FIG. 4 shows a fourth stage 400 in which the diastolic and systolic arterial pressures are affected. It is considered to be the full diastolic occlusion stage. In such a fourth stage 400, the force or pressure 145 being applied has a magnitude on the defined area 150 recorded in the force indicator 130 with a value of "60". The highest blood flow 125 shows expressions since the space in which the artery is embedded was decreased by the force in the systolic period 105, wherein such expressions are referred, among other things, to a sound 155 which, in this stage, is produced by the intermittent collisions, turbulences, and vibrations of arterial wall. The lowest blood volume or flow 120 disappears along with its expressions since the pressure or force applied 145 has been equaled to blood pressure or force in the diastolic period 110, time at which the lowest or diastolic blood pressure is determined in the artery segment.

Figure 5:
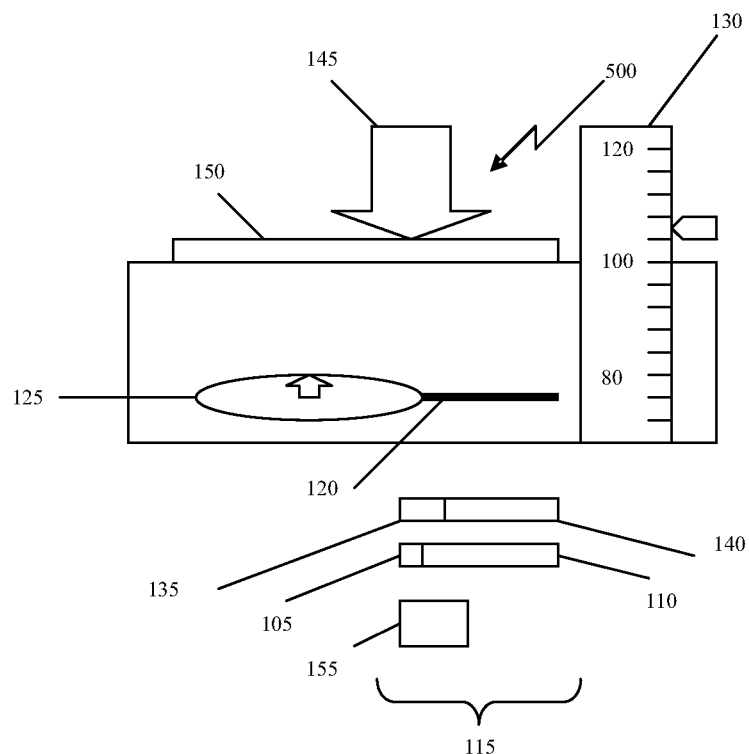

FIG. 5 shows a fifth stage 500 in which the systolic arterial pressure, diastolic occlusion, and blood flow reduction are affected with respect to the stage being shown in FIG. 5. This is considered to be the systolic pre-occlusive stage. In such fifth stage 500 the force or pressure being applied 145 has a magnitude on the defined area 150 recorded in the force indicator 130 with a value of "80". The highest blood flow or volume 125 shows expressions since the systolic period 105 changes, wherein such expressions are referred, among other things, to a sound 155 which is produced, in this stage, by the intermittent collisions, turbulences, and vibrations of arterial wall, which are reduced compared to the fourth stage 400, which is de diastolic occlusion stage. The lowest blood volume or flow 120 continues without expressions since the pressure or force applied 145 is higher than blood pressure or force in the diastolic period 110.

Figure 6:
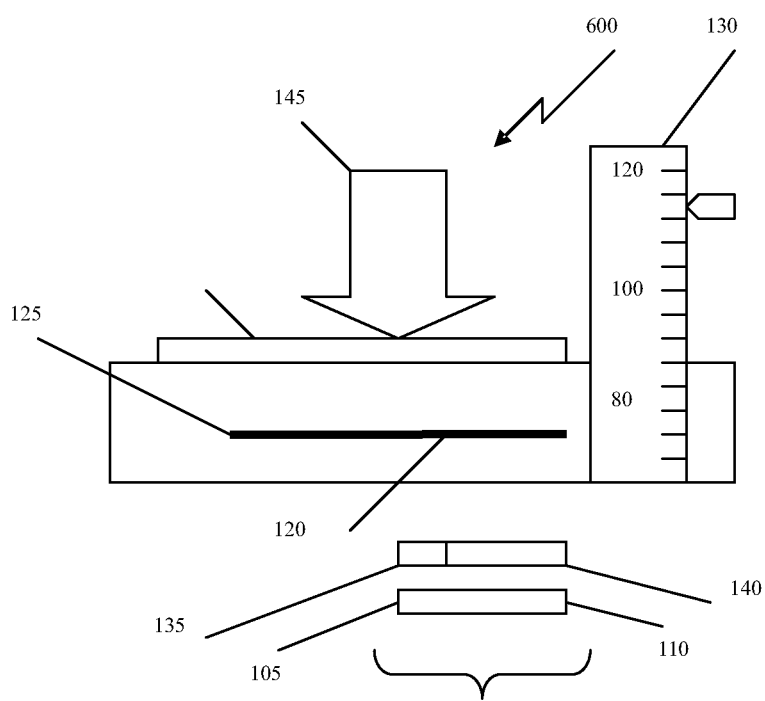

FIG. 6 shows a sixth stage 600 in which there is a full systolic and diastolic occlusion. In such sixth stage 600, the force or pressure being applied 145 has a magnitude on the defined area 150 recorded in the force indicator 130 with a value of "100". The highest blood flow or volume 125 shows no expressions since the pressure or force applied 145 has been equaled to blood force or pressure in the systolic period 105, wherein such expressions fully disappear, time at which the highest or systolic blood pressure is determined in the artery segment.

Figure 7:
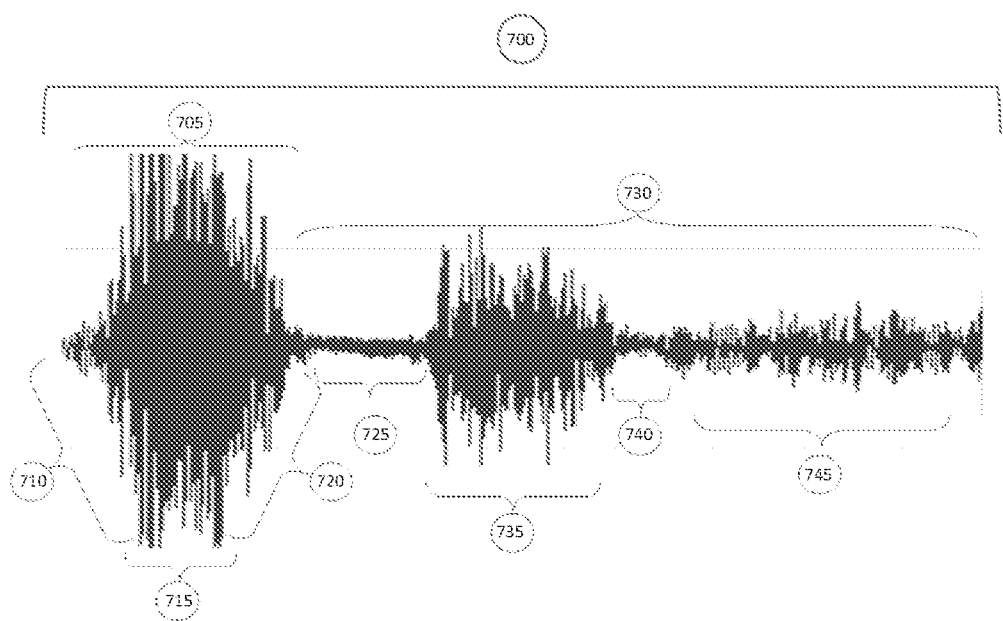
FIG. 7 shows an arterial cycle under normal physiological conditions having the features detected by a blood flow sensor.

In order to understand the arterial cycle, we refer now more specifically to FIG. 7, which shows an arterial cycle 700 under normal physiological conditions and having the characteristics detected by a blood flow movement sensor. The arterial cycle 700 is represented as a whole and consists of a distension stage and a higher arterial pressure corresponding to the systolic period 705. Here, the left ventricle ejects a blood volume to the arterial system, wherein arteries experience a rapid volume increase, distending until reaching a maximum pressure point as an adaptation response to such a blood volume increase. This phenomenon is referred to as adaptability stage 710 and it comes to an end in the distension limit stage 715 in which blood flow pressure and speed reach the maximum magnitude in the arterial cycle 700. The final systolic stage 720 follows then, in which blood pressure decreases and comes to an end at the beginning of the initial diastolic stage 725, which shows a sudden reduction in blood flow movement. It is at this point that the diastolic period 730 of arterial cycle 700 begins and it corresponds to a slow decrease in pressure fall and takes up the 75% of the full time of such an arterial cycle 700.

The diastolic period 730 consists of three stages. From these, a first stage corresponds to the initial diastolic stage 725 and continues with an alpha hemodynamic set 735 which, as the other hemodynamic sets, consists of parietal pressure, blood pressure, flow, and speed with a certain magnitude. In order to recognize them, Greek alphabet letters from alpha to the one with the highest magnitude are applied in a decreasing magnitude order letters beta, gamma, and delta are applied. Such an alpha hemodynamic set 735 is joined by low-amplitude frequencies 740 to a beta hemodynamic set 745. The diastolic period 730 ends with a sudden interruption of a hemodynamic set or of a low-frequency stage due to the sudden appearance of distension stage 710 of the systolic period 705 of the arterial cycle 700.

Figure 8:
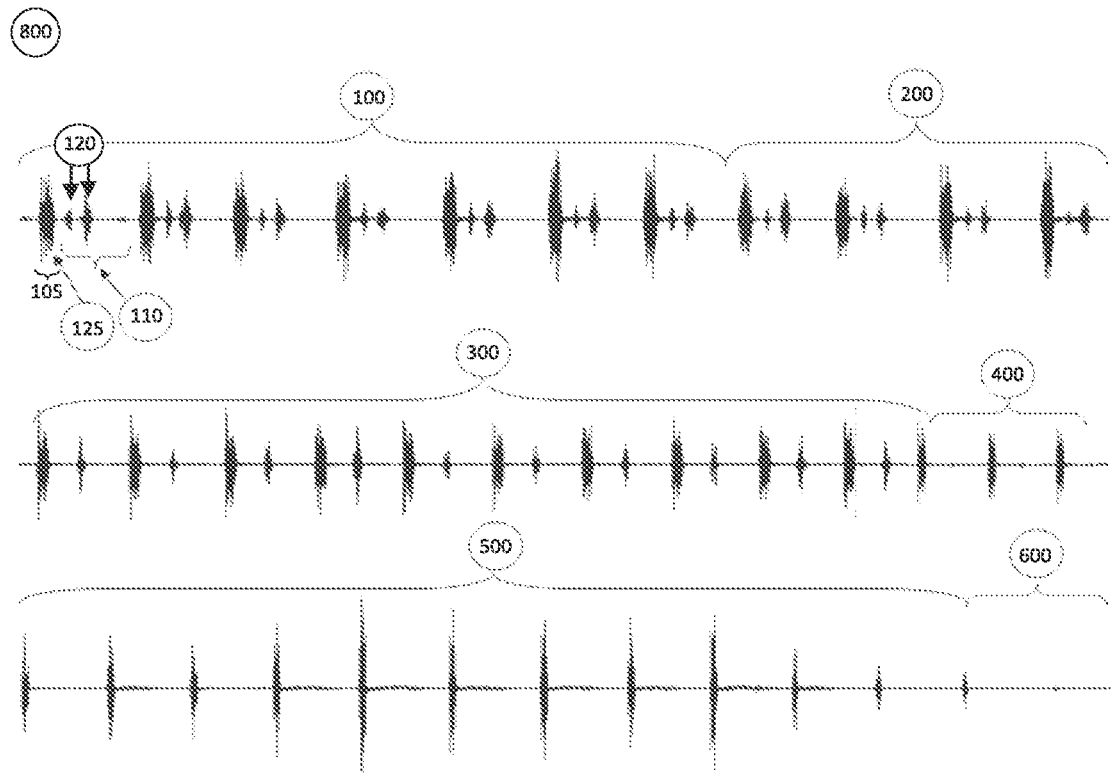
FIG. 8 shows a flow curve in the various stages produced by the effect of blood flow in systolic and diastolic periods when applying an external force.

Referring more specifically to FIG. 8, it shows a flow curve 800 in the various stages resulting from arterial expressions effect that have been previously depicted in FIGS. 1 to 6. In such a flow curve 800 the first stage 100 is shown without being affected by the external contact force and exhibiting the highest blood flow 125 corresponding to the systolic period 105 and the lowest blood flow 120 corresponding to the diastolic period 110; the second stage 200 being affected by the force, wherein only the highest blood flow 125 corresponding to the systolic period 105 is affected and the lowest blood flow 120 corresponding to the diastolic period 110 is not affected; in the third stage 300 there are expressions since the highest blood flow 125 corresponding to the systolic period 105 changes and the lowest blood flow 120 corresponding to the diastolic period 110 is also affected; in the fourth stage 400 there are expressions of change in the highest blood flow 125 corresponding to the systolic period 105, while the lowest blood flow 120 disappears along with its expressions, time at which the lowest or diastolic blood pressure is determined; in the fifth stage 500 there are expressions in the change of the highest blood flow 125 corresponding to the systolic period 105, which becomes greatly reduced, while the lowest blood flow 120 continues to be occluded; and, in the sixth stage 600 there are no expressions in the change of the highest blood flow 125 of the systolic period 105, since the external contact force ore pressure has been equaled to blood flow pressure or force of such a systolic period 105, time at which the highest or systolic blood pressure is determined and wherein the lowest blood flow 120 of the diastolic period 110 remains occluded.

Figure 9:
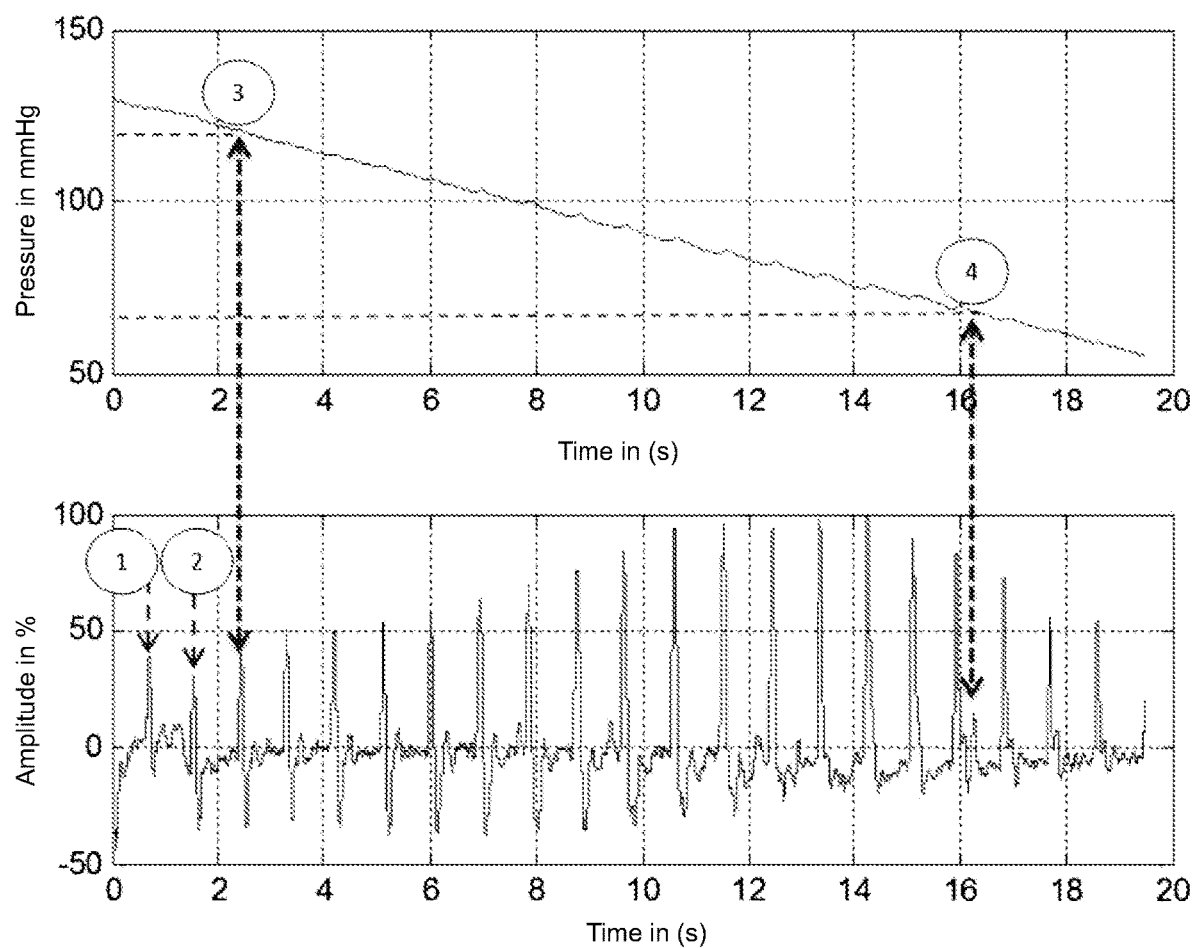
FIG. 9 shows the plot to measure diastolic arterial pressure using an indirect oscillometric method.

FIG. 9 From the drawings been shown, a plot of a pressure sensor signal is shown. In the drawing, once the artery had been occluded, pressure was released by recording the signal and an upper plot is seen which shows time depending on pressure in mercury millimeters, as well as a lower plot showing the time depending on pressure wave amplitude 3. Both plots show the wave in order to determine the systolic blood pressure of the systolic period of the arterial cycle 3. The appearance of the diastolic arterial pressure wave is seen in the arterial cycle diastolic period 4, as well as the first supramaximal wave 2 and the second supramaximal wave 1.

Figure 10:
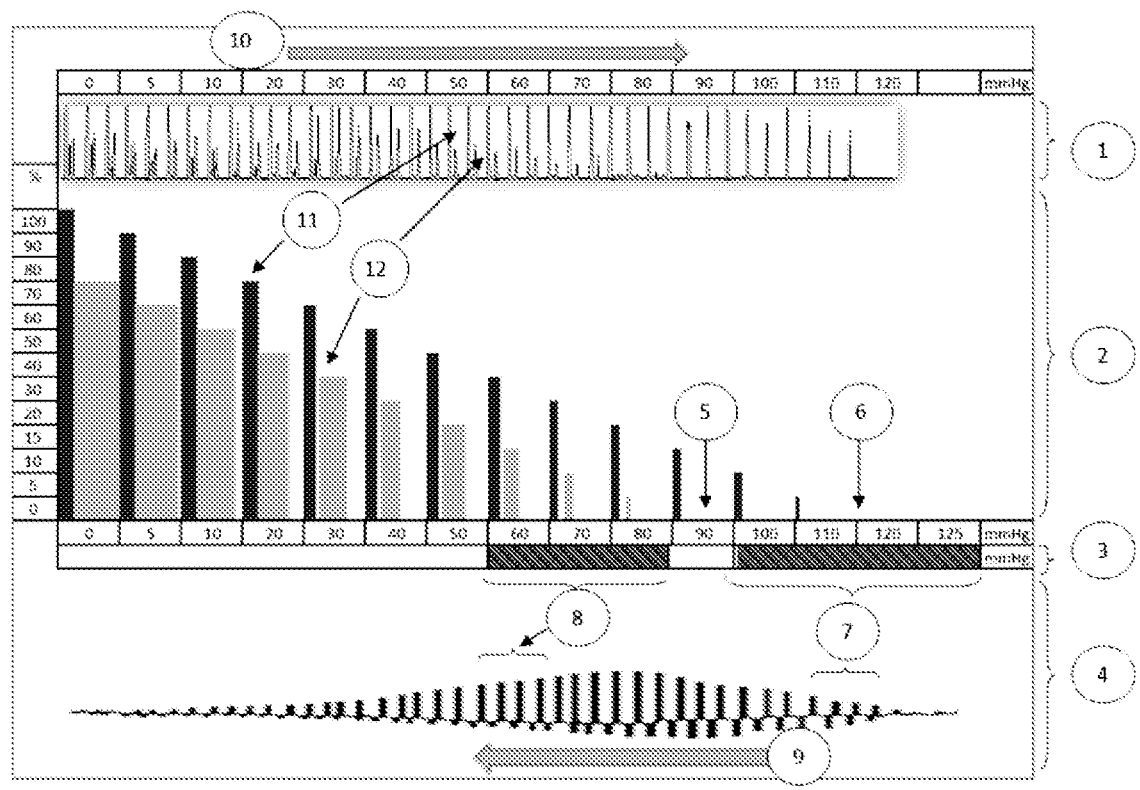
FIG. 10 shows the plot to measure diastolic and systolic arterial pressure using an indirect oscillometric method and with the diastolic arterial pressure measurement system using an indirect method.

FIG. 10 This plot shows diastolic and systolic arterial pressure measurement using an indirect oscillometric method 4, compared to the diastolic arterial pressure measurement system using an indirect method 2. It is seen a processed flow sensor signal plot 1 showing the systolic period 11, as well as the diastolic period 12, before a certain amount of force being applied; a bar plot of the arterial flow signal 2 which shows the systolic period 11 and the diastolic period 12, before a certain amount of force applied, shows the time to measure the diastolic arterial pressure with the diastolic pressure measurement system using an indirect method in the arterial cycle diastolic period 5, time to measure the systolic arterial pressure with the diastolic pressure measurement system using an indirect method in the arterial cycle diastolic period 6, measurement range of oscillometric systolic arterial pressure 7, pressure range for oscillometric diastolic arterial pressure 8.

Figure 11:
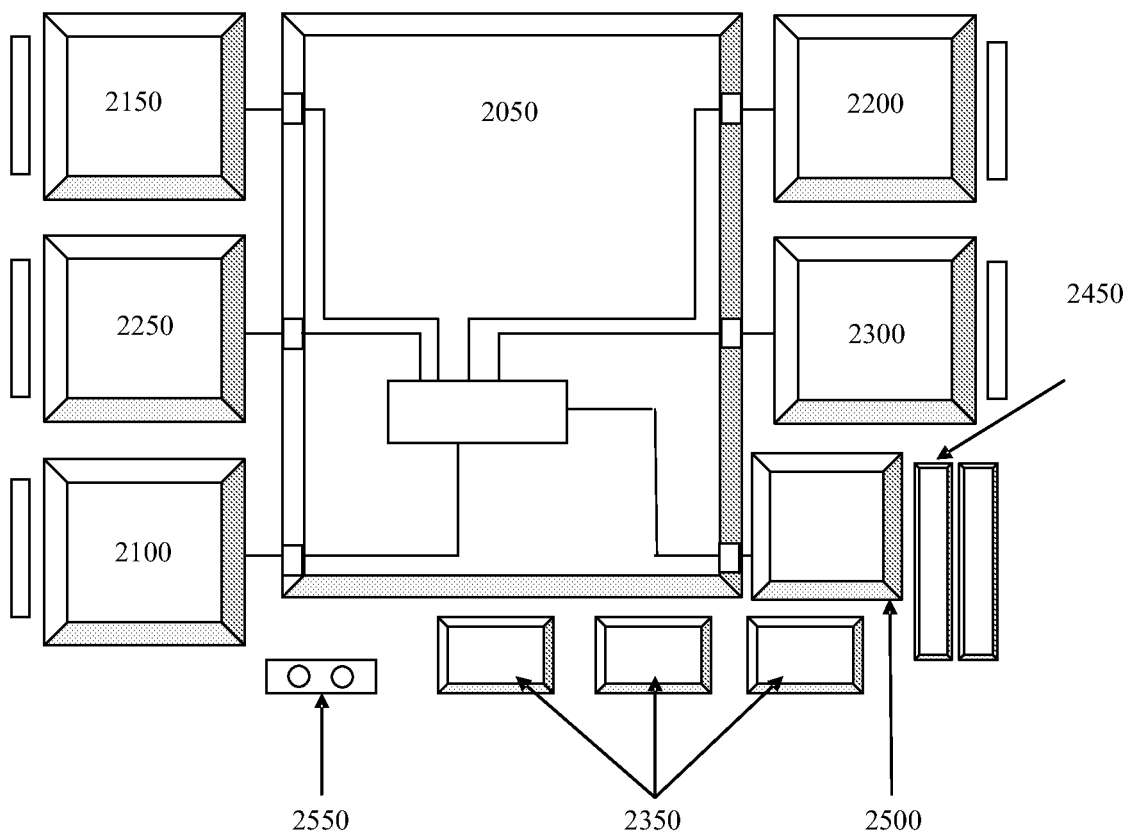
FIG. 11 is a block diagram of the electronic device to measure diastolic arterial blood pressure by its effects.

On the other hand, referring now to FIG. 11, it shows an electronic device for processing, analysis, and recording of arterial expression 2000. It consists of 6 units: a first main processing board unit 2050, a second pressure sensor board unit 2100, a third flow sensor board unit 2150, a fourth phonogram sensor board unit 2200, a fifth laser sensor board unit 2250, a six vibration sensor board unit 2300 wherein such an electronic board 2000 includes additional boards 2350, inlet or outlet ports 2400, memory 2450, screen outlet 2500, and feeding port 2550.

Figure 12:
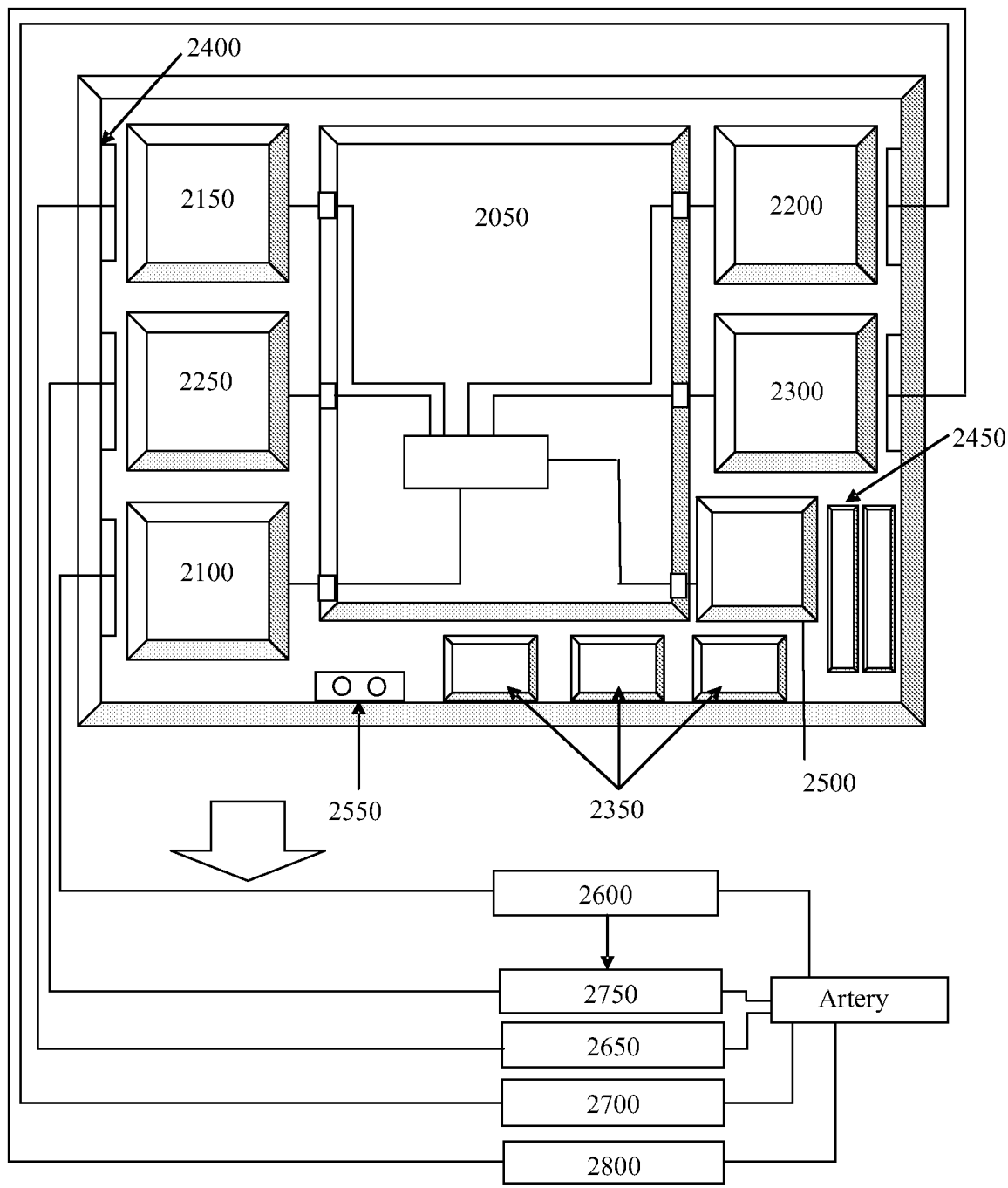
FIG. 12 is a perspective view of a block diagram showing the electronic device function when measuring diastolic arterial pressure.

Referring now more specifically to FIG. 12, it shows a block diagram of the operation of the elements to measure arterial pressure, including the internal elements of the electronic device for processing, analysis, and recording of arterial expression 2000. By applying an external pressure on the artery, the pressure sensor 2600 produces and sends a signal to such a board 2100, in parallel to the information received by the flow sensor 2650 and sent to such a board 2150. Such boards 2150 y 2100 prepare and send the signals to the main processing board 2050, wherein they are identified due to the fact that every arterial expression is represented by a specific signal in such an electronic board 2050. The signal corresponding to arterial expression detection is compared to the pressure sensor board signal 2100 in order to emit the diastolic arterial pressure measurement value.

The abovementioned course is followed in the case of the other sensors and boards. By applying an external pressure on the artery, pressure sensor 2600 produces and sends a signal to such a board 2100, in parallel to the information received by the sensor being used, which may be the phonogram sensor 2700, laser sensor 2750, and vibration sensor 2800 and sends it to the corresponding board 2200, 2250, 2300. At the same time, such boards 2200, 2250, 2300 and 2100 prepare and send the signals to the main processing board 2050, wherein they are identified due to the fact that every arterial expression is represented by a specific signal in such an electronic board 2050. The signal corresponding to arterial expression detection is compared to the pressure sensor board signal 2100 in order to emit the diastolic arterial pressure measurement value.

The present invention consists of a six-stage procedure and three means: The method to indirectly measure diastolic arterial pressure (MIPAD), which controls the tasks of a first device that applies a measured gradual external contact force (ApFGM); a second device for arterial expression sensing (SMA); and a third device that is a measuring and detection device of the arterial cycle diastolic and systolic period (MDCA).

Furthermore, the system and method for measuring arterial pressure by its effects allows measuring the systolic arterial pressure without overpressure due to heartbeats produced after arterial occlusion.

As previously stated, the present invention refers to a system and method for measuring arterial pressure by its effects, as well as for measuring systolic arterial pressure. Both measurements are made based on Arterial Expression (MA) observations, which is also referred to as Arterial Cycle Expression (MCA), and they are defined as the arterial wall and blood flow physical properties with or without affection of force applied on the artery. Blood flow arterial expressions are the arterial cycle systolic and diastolic period lasting time, pressure changes, flow movement changes, speed changes, temperature changes, volume changes, viscosity changes, mass and density changes; and arterial expressions based on the arterial wall are periods lasting time, changes in artery segments or cross section areas, perimeter changes, length changes, parietal pressure changes, and vibration changes.

The system and method for measuring arterial pressure by its effects comprises a device which must press the artery. Such a device is referred to as "device applying a measured gradual external contact force" and is defined as a device devoted to apply a force on the measurable artery in a gradual and measured manner, in order to obliterate it and know the magnitude of the force applied. Such a device is one of the most commonly used in the state of the art and it is preferably a cuff joined to a pressure sensor. In another embodiment, it may be a clip or tip. A device to detect arterial expressions referred to as "arterial expression sensor" is defined as a device that, upon being placed in a measurable artery segment, allows detecting and emitting the magnitude of a certain arterial expression during the time corresponding to an arterial cycle systolic period and diastolic period. In this embodiment, such a device is a flow sensor recording and emitting blood movement signals in the measurable artery segment and it has the following embodiments: pressure sensor, laser sensor, vibration sensor, and phonogram sound sensor. A device receiving the arterial expression magnitude emitted by the arterial expression sensor and the pressure sensor magnitude to emit the arterial pressure measurement value in the arterial cycle systolic period and diastolic period, is referred to as device for measuring and detecting the arterial cycle diastolic and systolic period. In this embodiment, we use an "electronic device for processing, analysis, and recording of arterial expressions", which comprises a circuitry central board in a complex electronic equipment and, in a variable fashion, with structural embodiment to be adapted to the structure of several measuring instruments for the same purpose, as well as board programming for the electronic device general interaction. It consists of a motherboard with critical subsystems, such as ports, connectors, system memory, sound card, flow sensor card, and pressure sensor board with the embodiments of laser sensor card, vibration sensor card, phonogram sound sensor card, and main processing card. The latter is the one in which signals received from the pressure sensor are processed with an oscillometric method or compared to the flow sensor, with the following embodiments of the laser sensor, vibration sensor, and phonogram sound sensor, in order to record and emit a systolic or diastolic pressure value based on the arterial expression of the arterial cycle systolic period and diastolic period. Such a device may be mechanical in nature through a graduated dial having indicators moving in response to pressure and decompression waves. A method to detect the arterial expression corresponding to the arterial cycle systolic period and diastolic period pressure is referred to as procedure to indirectly measure diastolic arterial pressure and it is defined as a procedure to identify and differentiate the arterial cycle systolic period and diastolic period based on the expressions resulting from the measurable artery with or without applying an external contact force, in order to measure diastolic arterial pressure by equaling the external force applied on the artery to the force applied by blood on the arterial wall by obliterating the artery in the arterial cycle diastolic period with an embodiment of arterial clearing in such arterial cycle period; furthermore, measuring systolic arterial pressure without affecting the pressure overload resulting from heartbeats after arterial occlusion and in the arterial cycle systolic period.

The integral development of the system and method for measuring arterial pressure by its effects comprises the following: First stage: The device applying a measured gradual external contact force (ApFGM) and the arterial expression sensor are placed on the measurable artery. The latter detects arterial expressions and sends them to the device measuring and detecting the arterial cycle diastolic period and systolic period (MDCA). The MDCA analyzes and differentiates the arterial expressions, determining high and low magnitudes depending on time with a cyclical character, establishing that an arterial expression containing a high and low magnitude depending on time is referred to as arterial cycle; based on the arterial cycle, a differentiation of the expressions magnitude depending on time is performed. A higher magnitude with lesser lasting time is obtained, which is referred to as systolic period, and an arterial expression with lesser magnitude and higher lasting time is also obtained, which is referred to as arterial cycle diastolic period. Using the device applying a measured gradual external contact force (ApFGM), an external contact force is applied, until the limit of not affecting the systolic arterial blood flow and pressure. This stage ends before affecting systolic blood flow with the external force.

Second stage: It consists of continuing to apply a gradual and measured external contact force, in addition to recording and analyzing the expressions of the arterial cycle systolic period and diastolic period through the devices used in the first stage until detecting arterial expressions corresponding to the systolic period which vary with respect to the physical properties that they exhibited during the first stage. Arterial expressions of the diastolic period continue to be the same as in the first stage since only the arterial cycle systolic period is affected by the external contact force applied.

Third stage: It consists of continuing to apply a gradual and measured external contact force, in addition to recording and analyzing the expressions of the arterial cycle systolic period and diastolic period through the devices used in the first stage until detecting that arterial expressions corresponding to the diastolic period vary with respect to the physical properties that they exhibited during the first stage, since the amount of force applied has affected the arterial blood flow in the arterial cycle diastolic period and the systolic period blood flow continues to be affected. This third stage is also referred to as diastolic pre-occlusion stage, since it is detected before the artery in the diastolic period is obliterated and it ends a little while before the full obliteration of the arterial cycle diastolic period is achieved.

Fourth stage: It consists of continuing to apply a gradual and measured external contact force, in addition to recording and analyzing the expressions of the arterial cycle systolic period and diastolic period through the devices used in the first stage until detecting that blood expressions corresponding to the diastolic period disappear since the external contact force applied obliterates the artery in the arterial cycle diastolic period, preventing that there is blood flow in this period. At this time, diastolic arterial pressure is measured by equaling the force applied in the measurable artery to the force magnitude applied by blood on the arterial wall based on the arterial expressions corresponding to the disappearance of the blood flow from the arterial cycle diastolic period. Systolic period arterial expressions are still present since blood force in such a period exceeds the contact force externally applied.

Fifth stage: It consists of continuing to apply a gradual and measured external contact force, in addition to recording and analyzing the expressions of the arterial cycle systolic period and diastolic period through the devices used in the first stage, detecting that the artery in the time corresponding to the diastolic period continues to be obliterated and in the systolic arterial period the flow considerably decreases with respect to the fourth stage. This fifth stage is also referred to as pre-occlusion systolic stage, since it ends a little while before the artery in the systolic period is obliterated.

Sixth stage: It consists of continuing to apply a gradual and measured external contact force and analyzing the expressions of the arterial cycle systolic period and diastolic period through the devices used in the first stage, and detecting that arterial expressions of the arterial cycle in its systolic period fully disappear since the artery is fully obliterated.

In addition to this sixth stage, upon detecting the disappearance of arterial expressions from arterial cycle systolic period, systolic arterial pressure is measured by equaling the force applied in the measurable artery to the force magnitude applied by blood on the artery wall with no overpressure due to heartbeats produced after arterial occlusion.

It is an embodiment to measure diastolic arterial pressure in this novel system and method for measuring arterial pressure by its effects to clear the artery, by removing the gradual external contact force to the previously occluded artery until the force applied by blood on the arterial wall in the arterial cycle diastolic period overcomes the external force applied.

Figure 13:
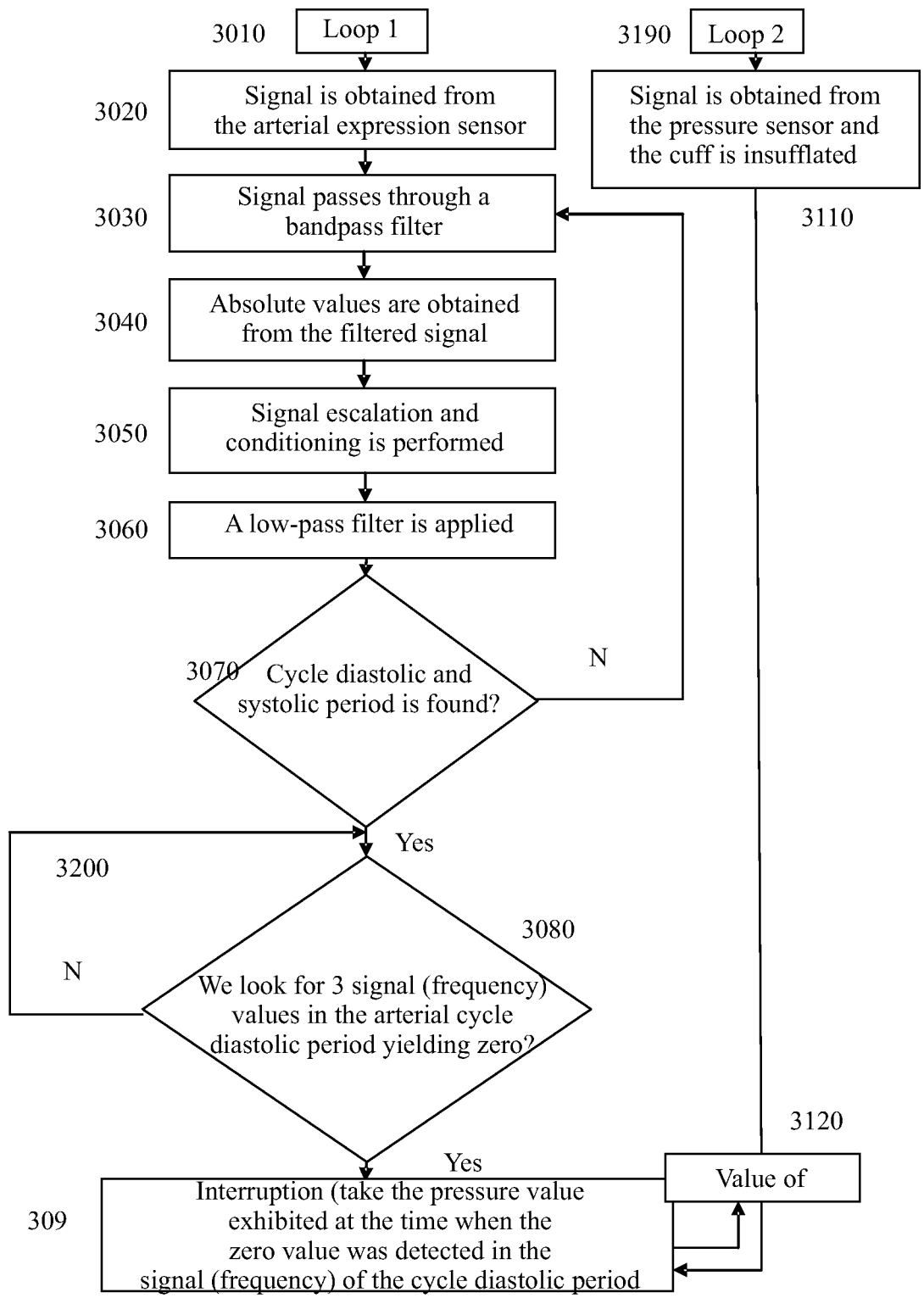
FIG. 13 shows a general diagram of the motherboard programming.

In a preferred embodiment of the invention there is a procedure to measure diastolic arterial pressure (MIPAD) using an indirect method which controls the activities of a device applying a measured gradual external contact force (ApFGM) which, in this embodiment, is a cuff joined to a pressure sensor; an arterial expression sensor (SMA) which in this embodiment is a flow sensor; a device for measuring and detecting arterial cycle diastolic period and systolic period (MDCA), which in this embodiment is an electronic motherboard basically operating, as seen in FIG. 13, in two loops and two subsystems, a first loop and subsystem 3190 to control and measure arterial pressure and a second loop and subsystem 3010 to collect, prepare and analyze the signal data received from the arterial expression sensor SMA 3020.

This embodiment of the invention includes measuring diastolic and systolic arterial pressure based on the diastolic and systolic periods, respectively, of an arterial cycle. Such measurements are performed through the procedure to measure diastolic arterial pressure using an indirect method (MIPAD) which controls the activities of the ApFGM, SMA, and MDCA devices, until obtaining the measurement of diastolic arterial pressure and additionally the systolic arterial pressure in the systolic period with no overpressure due to heartbeats produced after arterial occlusion.

The following procedure preferably uses as the device applying a measured gradual external contact force (ApFGM) a cuff joined to a pressure sensor and it uses as arterial expression sensor (SMA) in this embodiment a flow sensor. However, in other embodiments, it may be used as ApFGM any device allowing to apply pressure, such as a tip or a clip and, as SMA, any device allowing to detect and measure changes in pressure, changes in flow movement, changes in speed, changes in temperature, changes in volume, changes in viscosity, changes in mass and density, as well as changes in the artery segment or cross section area, changes in diameter, changes in perimeter, changes in length, changes in parietal pressure, and changes in vibrations.

In this embodiment, the system and method for measuring arterial pressure by its effects integrating MIPAD, ApFGM, SMA, and MDCA comprises the following stages:

MIPAD first stage: In this embodiment the cuff joined to a pressure sensor (ApFGM) is placed on the measurable artery. By means of a transducer, it measures the pressure applied to the cuff throughout the entire measurement process and in the distal end (in the direction of the hand) of the measurable artery. The flow sensor (SMA) is placed after the cuff and it has a transducer in order to receive arterial expressions and transform them in an electrical signal to be sent along with the signal sent by the pressure sensor to the electronic motherboard (MDCA). Such a MDCA filters and analyzes, for sampling and scanning purposes, the signals received from flow transducer, the profits and signal operating ranges are reviewed and adjusted at this time in order to be sent to the controller and to be processed therein. Motherboard programming in the second loop (as seen in FIG. 13) or subsystem consists in the electrical signal passage through a bandpass filter 3030. The resulting signal yields absolute values 3040 and a signal escalation 3050 is performed in order to be prepared. Finally, the signal passes through a low-pass filter 3060 and data analysis begins, the second loop and subsystem 3010 collects blood movement variation data delimiting the arterial cycle systolic period and diastolic period 3070 and measures any variation in each one of these periods. More particularly, such a processing consists of a signal differentiation based on its amplitude and frequency, whereby high and low magnitude signals are recorded depending on time and having a cyclical character. Based on the results of such an analysis and differentiation, it is established that an arterial expressions unit contains a high magnitude and a low magnitude of signals that are repeated depending on time. This unit is referred to as arterial cycle. The arterial cycle is composed of a higher magnitude with lesser lasting time, which is referred to as systolic period and an arterial expression with a lesser magnitude and a higher lasting time, which is referred to as arterial cycle diastolic period; with the cuff (ApFGM) placed in the patient arm at a certain speed during all pressure measurement process. An external contact force is applied, until the limit of not affecting systolic arterial blood pressure and flow. This stage ends before systolic blood flow is affected by the external force.

MIPAD second stage: It consists of continuing to apply a gradual and measured external contact force, in addition to recording and analyzing the expressions of the arterial cycle systolic period and diastolic period through the devices used in the first stage until detecting arterial expressions corresponding to the systolic period which vary with respect to the physical properties that were exhibited during the first stage. Arterial expressions of the diastolic period continue to be the same as in the first stage since only the arterial cycle systolic period is affected by the external contact force applied.

MIPAD third stage: It consists of continuing to apply a gradual and measured external contact force, in addition to recording and analyzing the expressions of the arterial cycle systolic period and diastolic period through the devices used in the first stage until detecting that arterial expressions corresponding to the diastolic period vary with respect to the physical properties that they exhibited during the first stage, since the amount of force applied has affected the arterial blood flow in the arterial cycle diastolic period and the systolic period blood flow continues to be affected. This third stage is also referred to as diastolic pre-occlusion stage, since it is detected before the artery in the diastolic period is obliterated and it ends a little while before the full obliteration of the arterial cycle diastolic period.

MIPAD fourth stage: It consists of continuing to apply a gradual and measured external contact force, in addition to recording and analyzing the expressions of the arterial cycle systolic period and diastolic period through the devices used in the first stage. Variation samples are provided every millisecond and their amplitudes are reviewed and compared until detecting that arterial expressions corresponding to the diastolic period disappear finding a zero or minimum amplitude range 3080 since the external contact force applied obliterates the artery in the arterial cycle diastolic period, preventing that there is blood flow in this period. Upon finding such a value, an interruption 3090 is activated, in which we take the pressure value found in the first loop and first subsystem 3120. This value is stored in the memory 3100 and corresponds to the diastolic pressure value resulting from equaling the force applied to the measurable artery to the magnitude of the force applied by blood on the arterial wall based on the arterial expressions corresponding to the disappearance of the blood flow from the arterial cycle diastolic period. If the signal amplitude variation in the diastolic period does not reach zero or the minimum range, the search continues in the third stage until such a value 3200 of the fourth stage is found, while systolic period arterial expressions continue to be present, since blood force in such a period exceeds the contact force that is externally applied.

MIPAD fifth stage: It consists of continuing to apply a gradual and measured external contact force, in addition to recording and analyzing the expressions of the arterial cycle systolic period and diastolic period through the devices used in the first stage, detecting that the artery at the time corresponding to the diastolic period continues to be obliterated and in the arterial systolic period the flow considerably decreases with respect to the fourth stage. Once the diastolic pressure value is recorded, the measurement follows and the second subsystem continues to collect blood variation data 3130. This fifth stage is also referred to as systolic pre-occlusion stage, since it ends a little while before the artery in the systolic period is obliterated.

MIPAD sixth stage: It consists of continuing to apply a gradual and measured external contact force, in addition to recording and analyzing the expressions of the arterial cycle systolic period and diastolic period through the devices used in the first stage and analyzing now the arterial cycle systolic period, wherein the samples of variations are reviewed and compared, detecting that arterial expressions of the arterial cycle in the systolic period fully disappear, finding a zero or minimum amplitude value range 3140, since the artery is fully obliterated. Once this value 3180 has been found, it corresponds to the systolic pressure and is stored and displayed in a screen along with the diastolic pressure value 3160. If the signal amplitude variation in the systolic period does not reach zero or the minimum range, the search continues until such a value 3210 is found.

This process lasts around 1 to 2 minutes when the cuff and the transducer are already placed in the arm. Once both pressures are found, the system goes back to the beginning of the two loops 3220 and a new measurement is prepared.

Additionally in this sixth stage, upon detecting the disappearance of the arterial expressions of the arterial cycle systolic period, systolic arterial pressure is measured by equaling the force applied to the measurable artery to the magnitude of the forced applied by blood on the arterial wall in the systolic period without overpressure due to heartbeats produced after arterial occlusion.

During the assessment stage of the diastolic pressure value measurement, the system verifies first if there are at least three values equal to zero or with a minimum range in the diastolic period 3080 and, secondly, at least three values equal to zero or with a minimum range in the systolic period 3140 and a decision is then made in order to determine the value or data found in the pressure sensor 3120, 3180 and determine the diastolic and systolic pressure value. For the first interruption 3090 in taking the pressure sensor storage value, we use the first value of the three values found in the diastolic period which are equal to zero. We then take the first value of the three values that are equal to zero in the systolic period for the second interruption 3150, which takes the pressure sensor value at this time.

In an alternative embodiment, additionally in this sixth stage, the MIPAD, using as SMA a pressure sensor and the oscillometric method; recording and analyzing signals. Pressure oscillation signal for arterial cycle systolic period in this stage disappears and only supramaximal pressure oscillation signals remain, since the external pressure being applied at this moment overcomes the pressure applied by blood on the arterial wall. However, the pulse wave in the adjacent artery transmits to the device applying a measured gradual external contact force the supramaximal arterial pulse waves being detected with the pressure sensor, which are considered to be as the minimum reference range or value or zero. In this MIPAD sixth stage, systolic arterial pressure is measured by equaling the force applied to the measurable artery to the magnitude of the force applied by the blood on the arterial wall.

With the various SMAs, it is required to previously define a minimum reference range or value or zero for every SMA.

In an alternative embodiment, it is possible to measure diastolic arterial pressure by using an arterial clearing method (MDA) using an indirect method in this novel system and method for measuring arterial pressure by its effects, by releasing the artery previously occluded from the gradual external contact force until allowing that the force applied by blood on the arterial wall in the arterial cycle diastolic period overcomes the external force applied.

MDA first stage: Using an electronic device for processing, analysis and recording of arterial expression, it records and analyzes arterial expression sensor board signals and the board of a device applying a measured gradual external contact force. Placing the arterial expression sensor and the device applying a measured gradual external contact force on the measurable artery, applying a force on the measurable artery until it is obliterated.

Furthermore, in this artery clearing stage, if the arterial expression sensor is a pressure sensor and the oscillometric method, only the signals from this sensor shall be recorded and analyzed, since the pressure sensor oscillation signal includes the arterial expression signal from the arterial cycle systolic period and diastolic period and the signal of the device applying a measured gradual external contact force.

MDA second stage: It consists of eliminating the measured gradual external force applied on the measurable artery, recording and analyzing signals in the same manner as in the arterial clearing first stage, including its additional form with the pressure sensor and oscillometric method, until detecting arterial expressions corresponding to the fact that the arterial systolic blood flow has overcame the external force applied.

MDA third stage: It consists of continuing to eliminate the measured gradual external force applied on the measurable artery, and recording and analyzing signals in the same manner as in the arterial clearing first stage, including its additional form with the pressure sensor and oscillometric method, until detecting arterial expressions corresponding to the fact that the arterial blood flow in the arterial cycle diastolic period has overcame the external force applied. At this time, diastolic arterial pressure is measured, which is able to overcome the external contact force applied on the artery.

In addition to this stage, in case that the arterial expression sensor is a pressure sensor and the method to be used is the oscillometric one; recording and analyzing signals using such an electronic device from the first stage based on the pressure sensor, since the pressure sensor oscillation signal includes the signal from the device applying a measured gradual external contact force. In this stage, oscillations of arterial pressure corresponding to the appearance of the arterial cycle diastolic arterial pressure are detected, and diastolic arterial pressure is measured since it has overcame the external force applied to the measurable artery by detecting the appearance of an oscillation in the diastolic period in addition to the one existing in the arterial cycle systolic period.

The same diastolic arterial pressure measurement may optionally be made in this third stage of arterial clearing by identifying the following arterial expressions and using the following sensors:

With the phonogram or flow sensor detect the appearance of the second sound or blood flow from the arterial cycle diastolic period, detect the disappearance of arterial wall intermittent collisions, detect the appearance of blood flow speed from the arterial cycle diastolic period, detect the appearance of arterial wall vibrations in the arterial cycle diastolic period, detect changes in the frequency spectrum density in the diastolic period of an arterial cycle, detect the artery diameter or volume variation in the diastolic period of an arterial cycle. With a temperature sensor, detect temperature variation in the arterial cycle diastolic period.

The invention claimed is:
1. An arterial pressure measurement system comprising:
an external contact force applying device applying an external contact force to a measurable artery;
a pressure sensor for measuring pressure of the applied external contact force and producing an electrical signal representing the measured pressure;
a flow sensor configured to be disposed on the measurable artery for detecting arterial expressions and producing an electrical signal representing the detected arterial expressions, wherein the flow sensor is selected from the group consisting of pressure sensor, laser sensor, vibration sensor and phonogram sensor;
a display; and
a motherboard in operable communications with the pressure sensor for receiving the electrical signal representing the measured pressure therefrom and with the flow sensor for receiving the electrical signal representing the arterial expressions therefrom, the motherboard being in operable communications with the display to convey information thereon, the motherboard being configured to:
engage the external contact force applying device to gradually apply the external contact force to the measurable artery;
during the gradual application of the external contact force, substantially continually receive the electrical signal representing the measured pressure from the pressure sensor;
during the gradual application of the external contact force, substantially continually receive the electrical signal representing the arterial expressions from the flow sensor when the arterial expressions are detected;
during the gradual application of the external contact force, perform signal differentiation on the received electrical signal representing the arterial expressions to identify an arterial cycle using amplitude, frequency and time of the electrical signal representing the arterial expressions such that high and low amplitudes depending on time are identified, where the arterial cycle comprises a systolic period defined by a systolic amplitude during a systolic time and a diastolic period defined by a diastolic amplitude that is lower than the systolic amplitude during a diastolic time that is longer than the systolic time;
during the gradual application of the external contact force and after the arterial cycle has been determined, identify a state of the arterial expressions, from the received electrical signals from the flow sensor during the diastolic period as being one of: not affected by the external contact force, affected by the external contact force but not occluded and occluded by the external contact force, where the state of occluded by the external contact force is identified when the received electrical signals representing the arterial expressions during the diastolic period have an amplitude that is zero or minimum amplitude;
after the arterial expressions are identified to be in the state of occluded by the external contact force during the diastolic period, determine a pressure applied by the external contact force from the received electrical signals representing the measured pressure at a time corresponding to the state of the arterial expressions being occluded by the external contact force during the diastolic period, the determined pressure representing a diastolic pressure;
during the gradual application of the external contact force and after the arterial cycle has been determined, identify a state of the arterial expressions, from the received electrical signals from the flow sensor during the systolic period as being one of: not affected by the external contact force, affected by the external contact force but not occluded and occluded by the external contact force, where the state of occluded by the external contact force is identified when the received electrical signals representing the arterial expressions during the systolic period have an amplitude that is zero or minimum amplitude;
after the arterial expressions are identified during the systolic period to be in the state of occluded by the external contact force, determine a pressure applied by the external contact force from the received electrical signals representing the measured pressure at a time corresponding to the state of the arterial expressions being occluded by the external contact force during the systolic period, the determined pressure representing a systolic pressure; and
provide the diastolic pressure and the systolic pressure to the display.

2. The arterial pressure measurement system according to claim 1, wherein measuring diastolic arterial pressure is performed in the diastolic period before the artery is fully occluded.

3. The arterial pressure measurement system according to claim 1, wherein the external contact force application device is an inflatable cuff or a clip or a tip.

4. The arterial pressure measurement system according to claim 1, wherein the flow sensor detects blood flow and the arterial expressions during the diastolic period and the systolic period.

5. The arterial pressure measurement system according to claim 1, further comprising a circuitry central board and a board programming programmed to operate the central board, the central board comprising the motherboard with subsystems selected from the group consisting of ports, connectors, system memory, at least one board for the flow sensor, a pressure sensor board, and a main processing board.

6. The arterial pressure measurement system according to claim 5, wherein the display device is a mechanical display having a graduated dial with indicators configured to move in response to the received electrical signals.

7. The arterial pressure measurement system according to claim 5, wherein the at least one board for the flow sensor comprises one of a pressure sensor board, a laser sensor board, a vibration sensor board, and a phonogram sensor board.

8. The arterial pressure measurement system according to claim 1, wherein the mother board is further configured to:
prior to performing signal differentiation on the received electrical signal representing the arterial expressions to identify the arterial cycle, determine based on the received electrical signal representing the arterial expressions that the arterial expressions are not affected by the gradual application of the external contact force.

9. The arterial pressure measurement system according to claim 1, wherein identifying the state of the arterial expressions during the diastolic period comprises:
identify portions of the received electrical signal representing the arterial expressions occurring during the diastolic period;
sample the portions of the received electrical signal representing the arterial expression occurring during the diastolic period at a rate of one sample every millisecond;
compare the sampled portions of the received electrical signal representing the arterial expressions to identify the sampled portions of the received electrical signal representing the arterial expression having zero or minimum amplitude representing the external contact force occluding the measurable artery during the diastolic period; and
wherein determining the pressure applied by the external contact force during the diastolic period comprises:
determine the received electrical signal representing the measured pressure occurring at a corresponding time as the identified sampled portions of the received electrical signal representing the arterial expressions,
wherein the diastolic pressure is the determined received electrical signal representing the measured pressure occurring at the corresponding time during the systolic period.

10. The arterial pressure measurement system according to claim 1, wherein identify the state of the arterial expressions during the systolic period comprises:
identify portions of the received electrical signal representing the arterial expressions occurring during the systolic period;
sample the portions of the received electrical signal representing the arterial expression occurring during the systolic period at a rate of one sample every millisecond;
compare the sampled portions of the received electrical signal representing the arterial expressions to identify the sampled portions of the received electrical signal representing the arterial expression having a zero or minimum amplitude representing the external contact force occluding the measurable artery during the systolic period; and
wherein determining the pressure applied by the external contact force during the systolic period comprises:
determine the received electrical signal representing the measured pressure occurring at a corresponding time as the identified sampled portions of the received electrical signal representing the arterial expressions,
wherein the systolic pressure is the determined received electrical signal representing the measured pressure occurring at the corresponding time during the systolic period.

11. The arterial pressure measurement system according to claim 9, wherein if the amplitude of the sampled portion of the received electrical signal representing the arterial expressions in the diastolic period does not reach zero or the minimum amplitude, the motherboard is configured to continue to identify, sample and compare until the amplitude of the sampled portion of the received electrical signal representing the arterial expressions in the diastolic period reaches zero or the minimum amplitude.

12. The arterial pressure measurement system according to claim 11, wherein identifying the state of the arterial expressions during the diastolic period further comprises:
after identifying the sampled portions of the received electrical signal representing the arterial expression having a zero or minimum amplitude, verify at least two identified sampled portions of the received electrical signal representing the arterial expression having amplitudes that are zero or the minimum amplitude during the diastolic period; and
if at least two identified sample portions of the received electrical signal representing the arterial expressions are verified, proceed with determining the received electrical signal representing the measured pressure occurring at a corresponding time as the identified sampled portions of the received electrical signal representing the arterial expressions.

13. The arterial pressure measurement system according to claim 10, wherein if the amplitude of the sampled portion of the received electrical signal representing the arterial expressions in the systolic period does not reach zero or the minimum amplitude, the motherboard is configured to continue to identify, sample and compare until the amplitude of the sampled portion of the received electrical signal representing the arterial expressions in the systolic period reaches the zero or the minimum amplitude.

14. The arterial pressure measurement system according to claim 13, wherein identifying the state of the arterial expressions during the systolic period further comprises:
after identifying the sampled portions of the received electrical signal representing the arterial expression having a zero or minimum amplitude, verify at least two identified sampled portions of the received electrical signal representing the arterial expression having amplitudes that are zero or the amplitude during the systolic period; and if at least two identified sample portions of the received electrical signal representing the arterial expressions are verified, proceed with determine the received electrical signal representing the measured pressure occurring at a corresponding time as the identified sampled portions of the received electrical signal representing the arterial expressions.

* * * * *